United States Patent [19]
Grätzel et al.

[11] Patent Number: 5,789,592
[45] Date of Patent: Aug. 4, 1998

[54] PHOSPHONATED POLYPYRIDYL COMPOUNDS AND THEIR COMPLEXES

[75] Inventors: Michael Grätzel, St-Sulpice; Oliver Kohle, Jouxtens; Mohammad K. Nazeeruddin, Ecublens; Péter Pechy, Lausanne; Francois P. Rotzinger, Chavornay; Stephan Ruile, Lausanne; Shaik Mohammad Zakeeruddin, Renens, all of Switzerland

[73] Assignee: Ecole Polytechnique Federale de Lausanne, Lausanne, Switzerland

[21] Appl. No.: 732,294

[22] PCT Filed: May 2, 1994

[86] PCT No.: PCT/IB94/00088

§ 371 Date: Oct. 30, 1996

§ 102(e) Date: Oct. 30, 1996

[87] PCT Pub. No.: WO95/29924

PCT Pub. Date: Nov. 9, 1995

[51] Int. Cl.[6] .......................... C07F 9/58; C07D 401/04; C09B 57/10; H01G 9/20
[52] U.S. Cl. .......................... 546/21; 546/257; 546/258; 546/263; 546/272.4; 546/273.4
[58] Field of Search ................................. 546/21

[56] References Cited

PUBLICATIONS

Chemical Abstracts, vol. 122,(No. 14), abst. No. 165,412m, Apr. 3, 1995.
Chemical Abstracts, vol. 123,(No. 12), abst. No. 148,949v, Sep. 18, 1995.
Chemical Abstracts, vol. 124,(No. 18), abst. No. 237,199p, Apr. 29, 1996.

Primary Examiner—Alan L. Rotman
Attorney, Agent, or Firm—Clifford W. Browning; Woodard, Emhardt, Naughton, Moriarty & McNett

[57] ABSTRACT

A compound in metal-free or metal complex form of formula (1) to (3) in which R is hydrogen or $C_{1-30}$ alkyl; X is hydrogen, halogen (preferably Cl or Br) or $C_{1-30}$ alkyl.

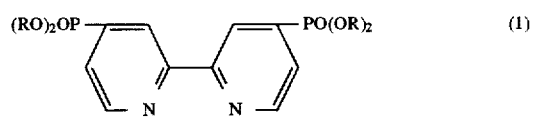

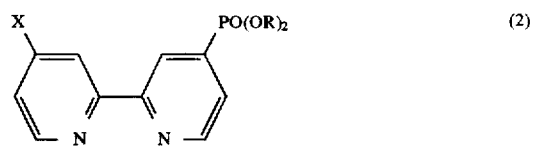

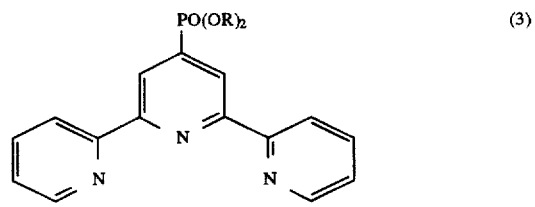

1 Claim, 2 Drawing Sheets

PHOSPHONATED POLYPYRIDYL COMPOUNDS AND THEIR COMPLEXES

CROSS-REFERENCE

This application is a 371 of PCT/11394/00088 filed May 2, 1994.

The present invention relates to the synthesis of a new class of phosphonated polypyridyl compounds and complexes, which have a number of applications. For example, the metal complexes can serve as ligands to form complexes with a variety of elements, in particular transition metals. The phosphonate groups of these polypyridyl complexes provide the transition metal complex with unique and desirable properties. Thus, the specific binding of the complex to oxidic functions e.g. the surface of oxides can be achieved. The formation of such surface bonds is very important.

Transition metal-phosphonated polypyridyl ligand complexes can be used as dyestuffs. Here the phosphonate group assists in immobilizing the dyestuff at the surface of the desired substrate. Such phosphonate modified complexes can be used in numerous systems.

Of particular interest is the application of these complexes as sensitizers in photogalvanic cells. In such a system, transition metal-phosphonated polypyridyl ligand complexes can be coated onto semiconducting oxides such as $TiO_2$. Due to the phosphonate groups, the adherence of the phosphonated polypyridyl ligand complex to the oxide surface is exceptionally strong, rendering these complexes particularly useful for the conversion of visible light into electric energy.

While the application of transition metal-phosphonated polypyridyl ligand complexes as sensitizers is of great practical importance, there are other applications (detailed later) where the exceptional properties of these polypyridyl compounds (for example in its non-metal complex form) and complexes having phosphonate binding groups can be used.

Thus, phosphonated bi- and poly- pyridyl complex can be grafted into metal surfaces to inhibit their corrosion. This is due to the formation of a chelate at the metal surface protecting the latter from attack by oxidants.

The adhesion of the phosphonate groups to matter present in living systems i.e. materials forming a bond with the skeleton of living beings such as calcium oxide, permits even more widespread applications of these ligands.

In particular these phosphonated polypyridyl ligand compounds may be used alone or in complexed form with elements such as radioactive technecium as diagnostic agents or remedies in tumoral diseases, as anticancer agents and as biosensors.

According to the invention, there is provided a bi- or polypyridyl phosphonate in metal free or metal complex form.

In particular, there is provided a compound, in metal-free or metal complex form of formula 1 to 3

(1)

(2)

(3)

in which
R is hydrogen or $C_{1-30}$ alkyl;
X is hydrogen, halogen (preferably Cl or Br) or $C_{1-30}$ alkyl.

Preferably, there is provided a metal complex containing at least one ligand which is a compound of formula 1 to 3, as defined above.

Preferably the metal of such a metal complex is a transition metal, more preferably selected from the group consisting of Ru, Os, Fe, Re or Tc, especially Ru(II), Os(II), Fe(II), Re(I) or Tc(I), (II), (III), (IV) or (V).

Further according to the invention there is provided a metal complex of formulae 4 to 13

$$[MLL'(X)_2] \quad (4)$$

in which
M is Ru(II), Os(II), Fe(II), Re(I) or Tc(I);
L is $L_a$ and L' is selected from $L_a$ $L_b$, $L_f$ $L_g$ $L_h$ or $L_i$; and
X is selected from the group of the ligands comprising NCS, Cl⁻, Br⁻, I⁻, CN⁻, NCO⁻, $H_2O$, $P(R_1)_3$, $P(R_1)_2$ (where $R_1$ is unsubstituted $C_{1-30}$alkyl, phenyl, unsubstituted or substituted by $C_{1-4}$alkyl, $C_{1-4}$alkoxy or halogen or pyridine, unsubstituted or substituted by one group selected from vinyl, primary, secondary and tertiary amines, OH and $C_{1-30}$alkyl);

$$[ML_3] \quad (5)$$

in which
M is as defined above and L is $L_a$ or $L_b$;

$$[MLL'_2] \quad (6)$$

in which
M is as defined above;
L is $L_a$ and
L' is $L_b$ or $L_f$ or $L_g$ or $L_h$ or $L_i$ defined below;

$$[ML_2L'] \quad (7)$$

in which
M is as defined above;
L is $L_a$; and
L' is $L_b$, $L_f$ $L_g$, $L_h$ or $L_i$ $$[ML_2] \quad (8)$$

in which
M is as defined above and
L is $L_c$ or $L_d$.

$$[MLL'] \quad (9)$$

in which
M is as defined above;

L is $L_c$ and
L' is from $L_e$ to $L_j$

|MLL'X|  (10)

in which

M and X are as defined above;
L is $L_a$ and
L' is from $L_e$ to $L_j$

|MLL'X|  (11)

in which

M and X are as defined above;
L is $L_c$ and
L' is from $L_a$, $L_b$, $L_f$ $L_g$, $L_h$ or $L_i$;

$[L_2M\{NCML'_2CN\}_2]$  (12)

in which

M is as defined above,
M' is Ru(II), Os(II), or Re(I);
L is selected from $L_a$ and
L' is $L_a$, $L_b$, $L_f$ $L_g$, $L_h$ or $L_i$;

$[LM\{NCML'_2CN\}_3]$  (13)

in which M and M' are as defined above.
L is selected from $L_c$ and
L' is from $L_a$, $L_b$, $L_f$ $L_g$ or $L_h$ or $L_i$;
whereby the symbols $L_a$ to $L_j$ are as defined below:

Ligand $L_a$

Ligand $L_b$

Ligand $L_c$

Ligand $L_d$

-continued

Ligand $L_e$

Ligand $L_f$

Ligand $L_g$

Ligand $L_h$

Ligand $L_i$ where R' is $C_{1-30}$ alkyl or phenyl

Ligand $L_j$ where each R independently is as defined above.

One aspect of the invention relates to the use of new transition metal complexes according to the invention in photovoltaic cells. These complexes can be coated on titanium dioxide films rendering the device effective in the conversion of visible light to electric energy.

Titanium dioxide films (layers) are known for their semiconductive properties and this property renders them useful for photovoltaic cells. However titanium dioxide has a large band gap; it does not absorb light in the visible region of the spectrum. For solar applications it is important that the titanium dioxide film be coated with a photosensitizer which harvests light in the wavelength domain where the sun emits light, i.e. between 300 and 2000 nm. Thermodynamic considerations show that conversion of solar energy into electricity is achieved in the most efficient fashion when all the emitted photons with wavelengths below 820 nm are absorbed by the photosensitizer. The optimal dye for solar conversion should therefore have an absorption onset around 800 nm and the absorption spectrum should be such that it covers the whole visible spectrum.

A second requirement for efficient solar light energy conversion is that the dyestuff after having absorbed light and thereby acquired an energy-rich state is able to inject with practically unit quantum yield, an electron in the conduction band of the titanium dioxide film. This requires that the dyestuff be attached to the surface of the titanium dioxide by means of suitable interlocking groups. The function of the interlocking group is to provide electronic coupling between the chromophoric group of the dyestuff and the conduction band of the semiconductor. This type of -electronic coupling is required to facilitate electron transfer between the excited state of the dyestuff and the conduction band. Suitable interlocking groups are π-conducting substituents such as carboxylate groups, cyano groups, phosphate groups or chelating groups with π-conducting character such as oximes, dioximes, hydroxy quinolines, salicylates and alpha keto enolates.

The electrons, photoinjected by the complex according to the invention, generate electrical current that is transmitted to an external circuit when a photovoltaic cell is operated.

According to the invention there is provided a photovoltaic cell comprising:
an electrically conductive layer (preferably light transmitting) deposited on a support (preferably glass plate, a transparent polymer sheet or a metal surface) to which one or more (preferably porous high surface area) titanium dioxide layers have been applied,
characterized in that a metal complex of formula 4 to 13 defined above is applied as a photosensitizer to the TiO$_2$ layer.

Still further according to the invention, there is provided a photovoltaic cell comprising:
i) two electrodes, at least one of which is transparent and has a visible light transmittance of at least 60%, the electrodes being arranged so as to define a receptacle between them, in which receptacle an electrolyte is located, one of the electrodes having a film of titanium dioxide (preferably high surface area) which is coated with a photosensitizer; and
ii) means for permitting the passage of an electrical current generated by the cell;
characterized in that the photosensitizer is a metal complex of formula 4 to 13 defined above.

Preferably a photovoltaic cell according to the invention comprises
i) an electrically conductive first plate to which a film of titanium dioxide is applied, (the film preferably having a thickness of 0.1–50 microns) and the film being coated with a photosensitizer; and
ii) an electrically conductive second plate with no TiO$_2$ film separated from the first plate by a thin layer of electrolyte, whereby the visible light transmittance of at least one of the plates is at least 60%; (preferably also for solar light);
characterized in that the photosensitizer is a metal complex of formula 4 to 13 defined above.

The second plate (also known as "the counterelectrode") may be coated with a thin layer (preferably up to 10 microns thickness) of an electrocatalyst. The role of the electrocatalyst is to facilitate the transfer of electrons from the counerelectrode to the electrolyte. A further possible modification of the counterelectrode is making it reflective to light that has first passed through the first plate and the electrolyte Further the outside of the glass plates may be coated with plastics like polystyrene (PS), polymethylmethacrylate (PMMA) or preferably polycarbonate (PC) to protect the TiO$_2$ layer, the dyestuff and the electrolyte against UV-light to give long term stability.

Preferably the electrolyte contains a redox system (acting as a charge transfer relay).

Preferably such systems include iodine/iodide solutions, bromine/bromide solutions, hydroquinone solutions or solutions of transition metal complexes capable of transferring defect electron (hole). The charge transfer relays present in the electrolyte transport electric charge from one electrode to the other. They act as pure mediators and undergo no chemical alteration during the operation of the cell.

It is preferable that the electrolytes in a photovoltaic cell according to the invention are dissolved in an organic medium so that the dyes applied to the titanium dioxide surface are insoluble therein. This has the advantage that the cell has a long-term stability.

Preferred solvents for the electrolyte include but are not limited to water and organic solvents such as $C_{2-15}$alcohols and mixtures thereof, non-volatile solvents such as 3-methyl (-2-oxazolidinone (NMO), 1,3-dimethyl-2-imidazolidinone (DMEN), propylene carbonate, ethylene carbonate and methyl pyrrolidinone, mixtures of non-volatile solvents with viscosity reducing solvents such as acetonitrile, ethylacetate or tetrahydrofuran. Additional solvents are dimethylsulfoxide or dichloroethane. Where miscible, mixtures of any of the above may be used.

Preferably the titanium dioxide films have a roughness factor greater than one, the roughness factor being defined as the ratio of true to apparent surface area. More preferably the roughness factor is 10–1000, most preferably 50–500. Preferably the titanium dioxide layers are built up on the surface of the conductive layer using one of two methods. One, the sol-gel method is described in Stalder and Augustynski, *J. Electrochem. Soc.* 1979, 126: 2007 and in Application Example A. The other, the "colloidal method" is described in Application Examples B and D.

In the sol-gel method it is preferable that only the last three, the last two or just the very top layer of the titanium dioxide is doped with a divalent or trivalent metal in an amount of not more than 15% doping by weight. However, the deposition of the pure dopant in form of a very thin top oxide layer can also be advantageous. In the latter cases a blocking layer is formed which impedes leakage current at the semiconductor-electrolyte junction..

All of the TiO$_2$ layers are formed by the sol gel process method described in Application Example A.

Preferably the number of TiO$_2$ layers deposited is 10–11. Preferably the total thickness of the TiO$_2$ film is from 5 to 50 microns (more preferably 10–20 microns).

The glass or polymer plate which is used for the transparent plate of the cell according to the invention is any transparent glass or polymer onto which a light transmitting electrically conductive layer has been deposited, such that the plate preferably has a visible light transmittance of 60–99%, more preferably 85–95%. Preferably the transparent conductive layer has a surface resistance of less than 10 ohms per square cms, preferably from 1 to 10 ohms per square cm. Preferably the transparent conductive layer used in a photovoltaic cell according to the invention is made of tin dioxide doped with ca. 0.8 atom percent of fluorine and this layer is deposited on a transparent substrate made of low-cost soda lime float glass. This type of conducting glass can be obtained from Asahi Glass Company, Ltd. Tokyo, Japan, under the brand name of TCO glass. The transparent conductive layer can also be made of indium oxide doped with up to 5% tin oxide, deposited on a glass substrate. This is available from Balzers under the brand name of ITO glass.

The photosensitizing layer may be produced by applying to the $TiO_2$ layer a dye according to the invention defined below.

The complexes according to the invention act as charge transfer sensitizers for nanostructured $TiO_2$ films (thickness 8–12 μm) of very high internal surface area (roughness factor ca. 1000), prepared by sintering of 15–30 nm-sized colloidal titania particles on a conducting glass support. The performance of cis-dithiocyanatobis (2,2'-bipyridyl-4,4'-phosphonated)-ruthenium(II) is especially good. Nanostructured $TiO_2$ films coated with a mono layer of 10 μ harvest visible light very efficiently, their absorption threshold being around 800 nm.

Conversion of incident photons into electric current is nearly quantitative over a large spectral range. These films can be incorporated in a thin layer regenerative solar cell equipped with a light-reflecting counterelectrode.

The open circuit voltage can be increased usefully by treating the dye-covered film with 4-tert butylpyridine. The effect of temperature on the power output and long term stability of the dye is also investigated. For the first time, a device based on a simple molecular light absorber attains a conversion efficiency commensurate with that of conventional silicon based photovoltaic cells.

While tris(2,2'-bipyridyl)ruthenium(II) and it homologues have been extensively investigated as redox sensitizers, very little is known about the excited state redox properties of the bis(2,2'-bipyridyl)ruthenium(II) analogues. The reason for this is that the excited state of these compounds is often too short-lived to allow for accurence of homogeneous bimolecular electron transfer reactions. However, heterogeneous charge transfer processes might still be initiated with such sensitizers since they can take place over a very short time scale. Apart from their chemical stability and ease of interfacial charge exchange with semiconducting solids, it has been found that these complexes have a large visible light harvesting capacity which is superior to that of the widely studied trisbipyridyl Ru(II) analogues, making them useful for use in a solar energy conversion device.

This invention also relates to uses for these compounds in all cases where binding of ligand through phosphonate to molecular or ionic species occurs as well as solids.

Areas of application are as follows:

1. Molecular species or polymers, DNA, RNA or other polynucleotides. Such applications include transition metal based photoactive or redox centers performing site-specific -change mutagenesis or photocleavage of nucleic acids.
2. Ionic applications for example those involving: $Zr^{4+}$, $Ca^{2+}$ and $Cu^{2+}$.. Such applications include bone targeted diagnosis or remedial for tumoric disease. $Zr^{4+}$ monolayer and multilayered engineering based on Zr phosphonate compounds for use as ultra thin condensers or insulators.
3. The use of oxides, for example $TiO_2$, ZnO, $Nb_2O_5$, $Fe_2O_3$, $In_2O_3$ and other semiconducting oxides. Phosphonated bi- and poly- pyridyl compounds will be used as ligand for transition metal sensitizers and redox relays for applications in photovoltaic cells, (one such cell is described above) biosensors and electrochromic devices.

One of the most common skeletal imaging agents is a $^{99m}$Tc-complex with diphosphonate ligands. Some of the clinically used diphosphonate ligands are pyrophosphonate, methylene diphosphonate, hydroxymethylene diphosphonate, 1-hydroxyethylidene disphosphonate. These ligands act as bridges between the technetium metal and the bone calcium. When administered, the above ligands with Tc metal, they accumulate in bone especially at sites of high calcium turnover in newly forming or cancerous bone. The relatively high uptake in newly forming bone is highly useful in diagnosing various bone cancers. The chemical structure and the oxidation state of the Tc complexes which are clinically used are not so far full elucidated.

The present invention includes the use of phosphonated polypyridyl ligands as a bridge between the $^{99m}$Tc metal and the bone calcium. Using ligands of formula 1 and 3 one can be able to make well-defined complexes of $^{99m}$Tc radiopharmaceuticals, which does not rapidly dissociate in vivo when these complexes administered can selectively accumulate in the target region without loosing radioactivity.

The invention will now be illustrated by the following examples.

EXAMPLE 1

Preparation of 2,2'-bipyridine-4,4'-bis (diethylphosphonate) a Compound of Formula 1

0.47 g of 4,4'-dibromo-2,2'-bipyridine (1.5 mmol) (as described in G. Maerker, F. H. Case, *J. Am. Chem., Soc.*, 1958, 80, 2745), 0.18 g of palladium tetrakis triphenylphosphine (0.15 mmole), 0.56 g of diethylphosphite (4.1 mmol) and 0.42 g of triethylamine (4.15 mmol) are measured into an argon filled 5 ml flask, equipped with a cold finger (10 cm) and magnetic stirrer. This is heated on a 98° C. oil bath for 3 hours. The reaction is monitored with TLC on silica gel plates, DCM: MeOH (10:1), Rf $L_a$=0.64. This is cooled back to room temperature and the solidified mixture is added to 8 ml of dichloromethane: methanol ( 1:1) and stirred for 10 min: This is evaporated to dryness under reduced pressure.

The residue is chromatographed on a silica gel column (gradient elution with DCM: MeOH and the fractions containing 2,2'-bipyridine-4,4'-bis(diethylphosphonate) ($L_a$) are evaporated to dryness (0.27 g, 53% (corrected for the unreacted 4,4'-dibromo-2,2'-bipyridine). From the earlier fractions unreacted starting material is recovered (0.1 g).

$^1$H-NMR(CDCl$_3$): 1.36 (12H, t, 7Hz), 4.20 (8H,m), 7.72 (2H, ddd, 14Hz, 5Hz, 1Hz), 8.77 (2H, dt, 14Hz, 1Hz), 8.84 (2H.dt, 5Hz, 1Hz) ppm. $^{13}$C-NMR (CDCl$_3$): 16.34 (d, $^3$J$_{C-P}$=5Hz), 62.79 (d, $^2$J$_{C-P}$=5Hz), 122.84 (d, $^2$J$_{C-P}$=9Hz), 125.65 (d, $^3$J$_{C-P}$=9Hz), 138.72 (d, $^1$J$_{C-P}$=186Hz), 149.58 (d, $^2$J$_{C-P}$=13Hz), 155.71 (d, $^3$J$_{C-P}$=14Hz) ppm. $^{31}$P-NMR (CDCl$_3$): 15.06 ppm. MS (IC): m/e (rel. int.) 429 (M+1, 44.82) 428 (M+, 5.7), 386 (19.8), 355 (5.0), 335 (5.9), 321 (3.2), 320 (24.8), 314 (9.0), 305 (4.9), 292 (100), 291 (4.9), 281 (9.3), 264 (4.5), 248 (5.3), 236 (13.9), 218 (8.1), 217 (3.2), 216(8.5), 211 (2.6), 188 (14.7), 176 (9.5), 157 (10.7), 151 (3.6), 147 (4.3), 109 (8.3), 98 (15.5). $C_{18}H_{26}N_2O_6P_2$ 428.36 calcd: C 50.47, H 6.12, N 6.54, P 14.46% found: C 50.67, H 6.25, N 6.69, P 14.50%

(Synthesis of diethyl-pyridine-3-phosphonate: T. Hirao, T. Masunaga, Y. Ohshiro, T. Agawa, Synthesis, 1981, 56)

EXAMPLE 2

Preparation of diethyl-4-bromo-2,2'-bipyridine-4'-phosphonate, a Compound of Formula 2.

2.0 g of 4,4'-dibromo-2,2-bipyridine (6.4 mmol), 0.9g of palladium tetrakistriphenylphosphine (0.8 mmol), 3.14 g of diethylphosphite (23 mmol) and 2.34 g of triethylamine (23 mmol) are measured into an argon filled 50 ml round bottom, flask, equipped with a cold finger (10 cm) and magnetic stirrer. This is heated on a 98° C. oil bath for 3 hours. The reaction is monitored with TLC on silica gel plates, DCM: MeOH (10:1), Rf-Lb=0.73. This is then cooled back to room temperature, and then the solidified mixture is added to 25 mls of methanol, stirred for 10 min. and evaporated to dryness under reduced pressure.

The residue is chromatographed on a silica gel column (gradient elution with DCM: MeOH), the fractions containing diethyl-4-bromo-2,2'-bipyridine-4'-phosphonate ($L_b$) are evaporated to dryness, resulting a colorless oil (0.79 g; 40% corrd.).

From more polar fractions, 2,2'-bipyridine4,4'-bis(diethylphosphonate) (La) (0.97 g; 44% corrd.) is isolated as a white solid. From earlier, more apolar fractions unreacted starting material is recovered (0.34 g; 6%).

$^1$H-NMR (CDCl$_3$): 1.20 (6H, t, 7Hz), 4.05 (4H, m), 7.32 (1H, dd, 5Hz, 2Hz), 7.56 (1H, ddd, 13Hz, 5Hz, 2Hz), 8.32 (1H, d, 5Hz), 8.44 (1H, d, 2Hz), 8.61 (1H, dt, $^3J_{P-H}$=15Hz, 1.5Hz), 8.65 (1H, dt, 5Hz, 1.5Hz) ppm. $^{13}$C-NMR(CDCl$_3$): 16.02 (d, $^3J_{C-P}$=6Hz), 62.39 (d, $^2J_{C-P}$=6Hz), 122.52 (d, $^2J_{C-P}$=10Hz), 124.18(s), 125.34 (d, $^3J_{C-P}$=8Hz), 126.87(s), 133.49 (s), 138.44 (d, $^1J_{C-P}$=187Hz) (149.10 (d, $^2J_{C-P}$=13Hz), 149.64(s), 154.78 (d, $^3J_{C-P}$=13Hz), 156.05(s) ppm. $^{31}$P-NMR (CDCl$_3$): 14.82ppm. MS (EI): m/e (rel. int.) 373 (2.5), 372 (9.3), 371 (3.3), 370 (M$^+$, 8.8) 328 (20.9), 326 (20.0), 299 (17.5), 297 (17.8), 264 (10.4), 262 (16.5), 237 (12.3), 236 (100), 235 (23.2), 234 (98.9), 208 (9.4), 127 (6.8). $C_{14}H_{16}N_2BrO_3P$ 371.17 calcd: C 45.30, H 4.34, Br 21.53, N 7.55, P 8.34% found: C 45.35, H 4.38, Br 21.41, N 7.61, P 8.39%

EXAMPLE 3

Preparation of diethyl-2,2':6,2"-terpyridine-4-phosphonate, a Compound of Formula 3

2.55 g of 4'-bromo-2,2':6'2"-terpyridine (8.2mmol), 0.6 g of palladium tetrakistriphenylphosphine (0.5 mmol), 1.9 g of diethylphosphite (2.04 g, 15 mmol) and 1.52 g of triethylamine (2.1 ml, 15 mmol) are measured into an organ filled 50 ml round bottom flask, equipped with a cold finger (19 cm) and magnetic stirrer. This is heated on a 95° C. oil bath for 3 hours and cooled back to room temperature. The solidified mixture is added to 25 ml of methanol, chromatographed on a silica gel column (gradient elution with DCM: MeOH). The fractions containing diethyl-2,2':6'2"-terpyridine4'-phosphonate are evaporated to dryness (1.7 g). From earlier fractions unreacted starting material is recovered (0.57 g). 72.3% (corrected for the unreacted 4'-bromo-2,2':6',2"-terpyridine).

mp: 140° C./152° C. (ethanol) $^1$H-NMR (CDCl$_3$): 1.35 (6H, t, 7Hz), 4.21 (4H, m), 7.30 (2H,ddd, 7.5Hz, 5Hz,, 2Hz), 7.82 (2H, dt, 8Hz, 2Hz), 8.56 (2H, d, 8Hz), 8.68 (2H, d, 4.5Hz), 8.82 (2H, d, $^3J_{P-H}$=14Hz) ppm. $^{13}$C-NMR(CDCl$_3$): 16.29 (d, $^3J_{C-P}$=6Hz), 62.58 (d, $^2J_{C-P}$=6Hz), 121.11(s) 122.58 (d, $^2J_{C-P}$=10Hz), 124.00(s), 136.70(s), 139.54 (d, $^1J_{C-P}$=186Hz), 149.20(s), 155.27 (d, $^4J_{C-P}$=2Hz), 155.79 (d, $^3J_{C-P}$=14Hz) ppm. $^{31}$P-NMR (CDCl$_3$): 15.59ppm. MS (EI): m/e (rel. int.) 370 (6.8), 369 (M$^+$, 29.1) 339 (2.8), 324 (1.1), 312 (2.0), 308 (1.0), 262 (2.2), 261 (11.5), 260 (6.3), 259 (2.3), 234 (18.6), 233 (100), 232 (7.6), 221 (1.5), 156 (2.0), 155 (5.1), 130 (2.3), 129 (12.5), 127 (15.9), 105 (2.3), 102 (2.7), 101 (2.1), 75 (2.7). $C_{19}H_{20}N_3O_3P$ 369.36 calcd: C 61.79, H 5.46, N 11.38, P 8.39% found: C 61.86, H 5.42, N 11.27, P 8.50%

EXAMPLE 4

Preparation of 2,2':6',2"-terpyridine-4,4',4"-tricarboxylic acid, a compound of formula 4

A solution of 278 mg of 4,4',4"-trimethyl-2,2':6',2"-terpyridine (1 mmol) (prepared by analogy to P. E. Posevear, W. H. F. Sasse, *J. Het. Chem.*, 1971, 8, 483) in pyridine abs. (3.7 ml) is oxidized with a solution of 2.7 g of tetrabutylammonium permanganate (7.5 mmol) in 5.6 ml of pyridine at 90° C. during 1 hour 45 min. This is filtered at room temperature, the solvent is evaporated to dryness, the residue treated successively with water (2×10 ml), benzene (2×10 ml) and dichloromethane (10 ml). The residue is taken up in water (10 ml), extracted with ether (3×5 ml). The water phase is evaporated to dryness, and oxidized further with nitric acid (70%, 5 ml) at 140° C. supplying the nitric acid (4×3ml) in every 12 hours.

The acid is evaporated at the above temperature to dryness. After alkaline and acidic treatment, a white powder separates at pH=3.5, filtered washed with water and dried (137 mg). According to the $^1$H- and $^{13}$C-NMR spectra (in D$_2$O/NaOH) the product is a 4:1 mixture of 2,2':6',2"-terpyridine-4,4',4"-tricarboxylic acid and 4-methyl-2,2',6', 2"-terpyridine-4',4"-dicarboxylic acid.

EXAMPLE 5 a) Synthesis of [RuL$_2$(Cl)$_2$] where L is 2,2'-bipyridine-4,4'-bis(diethylphosphonate).

This complex is synthesized by refluxing 52.3 mg (0.2 mmol) of RuCl$_3$ 3H$_2$O and 171.2 (0.4 mmol) of ligand 2,2'-bipyridine-4,4'-bis(diethylphosphonate) in 15 ml of DMF for 6 hours. After allowing it to come to room temperature, the product is filtered through sintered glass crucible. The filtrate is evaporated under vacuum and the [RuL$_2$(Cl)$_2$] is precipitated with 1:1 acetone/diethyl ether mixture. The crystals are filtered off and washed two times with 1:1 acetone/diethyl ether mixture followed by treating with anhydrous diethyl ether. After drying in vacuum the yield is 76%.

b) Synthesis of [RuL$_2$Cl$_2$] where L is 2,2'bipyridine 4,4'-bis (diethylphosphonic acid), a compound of formula 4

The compound 5b) is hydrolyzed by refluxing it in 4N HCl for 6 hours, under nitrogen. After this period the solvent is evaporated on a rota-vap. The resulting solid is dissolved in water and evaporated the same way. This procedure is repeated two times in order to remove HCl completely.

c) Synthesis of [RuL$_2$(NCS)$_2$] where L is 2,2'-bipyridine-4, 4'-diphosphonic acid, a compound of formula 4.

205 mg of (0.2 mmol) [RuL$_2$(Cl)$_2$] are dissolved in 20 ml of DMF, under reduced light. 243 mg (3 mmol) of sodium thiocyanate are separately dissolved in 2 ml of water and subsequently added to the above solution. Then the reaction mixture is heated to reflux for 3 hours under a nitrogen atmosphere, while maintaining magnetic stirring. After this time, the reaction mixture is allowed to cool and filtered through sintered glass crucible.

The filtrate is evaporated on a rotary evaporator and the resulting solid is dissolved in water and filtered. To the filtrate dilute $HClO_4$ (0.01 mol) is added until the pH of the solution is 1–2. At this pH the complex precipitates completely and the flask is kept in refrigerator for 12 hours. After allowing the reaction flask to come to room temperature, the resulting solid is collected on a sintered crucible and washed throughly with acetone followed by diethyl ether. The compound is dried under vacuum at room temperature for 3 hours.

EXAMPLE 6 a) Synthesis of $[RuCl_2(DMSO)_4]$ where the DMSO= dimethylsulfoxide.

1 g. of ruthenium trichloride trihydrate is refluxed in 5 ml of DMSO for one hour. After this period of time, the addition of acetone gives a yellow precipitate. The yellow complex which separates off is filtered off, washed with acetone and diethylether. The yield is about 80%.

b) Synthesis of $[Ru(L)Cl_2(DMSO)_4]$ where L is 4,4'-methyl-2,2'-bipyridine.

One equivalent of $[RuCl_2(DMSO)_4]$ and one equivalent of 4,4'-dimethyl-2,2'-bipyridine are refluxed in chloroform for one hour. The solution is cooled and the solvent is removed on a rotary evaporator. The resultant solid is dissolved in acetone and filtered. Addition of diethyl ether to the filtrate gives a yellow precipitate. This collected on a glass frit, washed with ether and vacuum dried.

c) Synthesis of $[Ru(L)(L')(Cl)_2]$ where L is 4,4'-dimethyl-2,2'-bipyridine and L' is 2,2'-bipyridine-4,4'-bis(diethylphosphonate).

One equivalent of $[RuL(Cl_2)(DMSO)_2]$, where L is 4,4'-dimethyl-2,2'bipyridine and one equivalent of 2,2'-bipyridine-4,4'bis-(diethylphosphonate) are placed in dimethyl formamide and the mixture is refluxed for 3–4 hours in the dark. After this period, the reaction mixture is filtered through sintered glass crucible. The filtrate is evaporated and the resultant solid is washed with a 1:1 mixture of acetone/ether and then washed with diethyl-ether and vacuum dried.

d) Synthesis of $[Ru(L)(L')Cl_2]$ where L is 4,4'-dimethyl-2,2'-bipyridine and L' is 2,2'-bipyridine-4,4'-diphosphonic acid.

This is prepared by an analogous procedure to that described in Example 5b)

e) Synthesis of $[Ru(L)(L')(NCS)_2]$ where L is 4,4'-dimethyl-2,2'-bipyridine and L' is 2,2'-bipyridine-4,4'-bis(diethylphosphonate).

This is prepared in an analogous procedure to that described in Example 5c).

EXAMPLE 7 a) Synthesis of $[RuL_3]$ where L is 2,2'-bipyridine-4,4'-bis(diethylphosphonate), a compound of formula 5.

This is prepared by refluxing one equivalent of $RuCl_3$ $3H_2O$ and three equivalents of 2,2'-bipyridine4,4'-bis(diethylphosphonate) in DMF for 5 hours under nitrogen. After this period the solvent is evaporated on a rota-vap and the resulted solid is dissolved in aqueous solution of 4N HCl and refluxed for 6–8 hours. The solvent is evaporated on a rota-vap and the resulting solid is dissolved in 0.01 m aqueous solution of NaOH. The pH of this solution is lowered to 1–2 by the addition of dilute $HClO_4$. The flask is kept in refrigerator for 12 hours after allowing it to come to room temperature, the precipitate is collected on a sintered crucible and washed thoroughly with acetone followed by diethyl ether. The compound is dried under vacuum at room temperature for 3 hours.

EXAMPLE 8 a) Synthesis of $[RuL'_2(Cl)_2]$ where L' is selected from $L_h$, where R is hydrogen or $C_{1-15}$ alkyl group is prepared by an analogous procedure to that described in Example 5a)

b) Synthesis of $[RuLL'_2]$ where L is 2,2'-bipyridine4,4'-bis(diethylphosphonate), and L' is selected from $L_h$, where R is hydrogen or $C_{1-15}$ alkyl group (a compound of formula 6.)

This is prepared by refluxing one equivalent of $[RuL'_2(Cl)_2]$ and 1.5 equivalent of 2,2'-bipyridine-4,4'-bis(diethylphosphonate) in DMF for 5 hours under nitrogen. After this period the solvent is evaporated on a rota-vap and the resulted solid is dissolved in aqueous solution of 4 n HCl and refluxed for 6–8 hours. The solvent is evaporated on a rota-vap and the resulting solid is recrystallized from ethanol diethyl ether mixture. The compound is dried under vacuum at room temperature for 3 hours.

EXAMPLE 9 a) Synthesis of $[RuL_2(Cl)_2]$ where L is 2,2'-bipyridine4,4'-bis(diethylphosphonate), is prepared by an analogous procedure to that described in Example 5a)

b) Synthesis of $[Ru(L)_2(L')]$ where L is 2,2'-bipyridine-4,4'-bis(diethylphosphonate), and L' is selected from $L_h$, where R is hydrogen or $C_{1-15}$ alkyl group, a compound of formula 7.

This is prepared by refluxing one equivalent of $[RuL_2(Cl_2)]$ and 1.5 equivalent of $L_h$ in DMF for 5 hours under nitrogen. After this period the solvent is evaporated on a rota-vap and the resulted solid is dissolved in aqueous solution of 4N HCl and refluxed for 6–8 hours. The solvent is evaporated on a rota-vap and the resulting solid is dissolved in 0.01 m aqueous solution of NaOH. The pH of this solution is lowered to 1–2 by the addition of dilute $HClO_4$. The flask is kept in refrigerator for 12 hours, after allowing it to come to room temperature the precipitate is collected on a sintered crucible and washed throughly with acetone followed by diethyl ether. The compound is dried under vacuum at room temperature for 3 hours.

EXAMPLE 10

Synthesis of $[RuL_2]$ where L is diethyl-2,2':6',2"-terpyridine-4'-phosphonate, a compound to formula 8 a) This is prepared by refluxing one equivalent of $RuCl_3$, $3H_2O$ and slightly more that two equivalents of diethyl-2, 2':6',2"-terpyridine-4'-phosphonate in DMF for 4 hours under nitrogen. After this period the solvent is evaporated on a rota-vap and the resulting solid is recrystallized from ethanol diethyl ether mixture. The compound is dried under vacuum at room temperature for 3 hours.

b) Synthesis of $[RuL_2]$ where L is diethyl-2,2':6',2"-terpyridine-4'-phosphonic acid a compound of formula 8.

This is prepared by an analogous method to that described in Example 5c).

EXAMPLE 11 a) Synthesis of $[RuL(Cl)_3]$ where L is diethyl-2,2':6',2"-terpyridine4'-phosphonate.

This is prepared by refluxing 200 mg (0.77 mmol) of $RuCl_3.3H_2O$ and [284] mg (0.77 mmol) of the ligand $L_c$ in ethyl alcohol, under nitrogen for one hour. After this period the reaction mixture is allowed to cool and the resulted precipitate are collected on a sintered glass crucible. The solid is washed thoroughly by ethyl alcohol followed by diethyl ether and dried under vacuum to give a yield over 90%.

b) Synthesis of $[RuLL']$ where L is diethyl-2,2':6',2"-terpyridine-4'-phosphonate and L' is selected from the ligand $L_e$, where R is hydrogen or $C_{1-15}$ alkyl group (a compound of formula 9).

This is prepared by refluxing one equivalent of [RuL(Cl)$_3$] where L is 4-(bis)ethyl phosphonated-2,2':6',2"-terpyridine and one equivalent of Le where R is H or alkyl (C$_{1-15}$) group in DMF for 3 hours under nitrogen. After this period the solvent is evaporated on a rota-vap and the resultant solid is recrystallized from ethanol diethyl ether mxiture. The compound is dried under vacuum at room temperature for 3 hours

EXAMPLE 12 a) Synthesis of [RuL(Cl)$_3$] where L is diethyl-2,2':6',2"-terpyridine4'-phosphonate. This is prepared by an analogous procedure to that described in Example 11a b) Synthesis of [RuLL'(CI) where L is 4-(bis)ethylphosphonated-2,2':6',2"-terpyridine and L' is 4,4'-dimethyl-2,2'-bipyridine.

This is prepared by refluxing 200 mg of (0.35 mmol) of the product of Example 12a and 83 mg of (0.45 mmol) 4,4'-dimethyl 2,2'-bipyridine in 20 ml of DMF for 6 hours, under nitrogen. After this period the reaction mixture is allowed to cool and filtered through sintered glass crucible. Most of the solvent DMF is evaporated on a rota-vap and the complex in precipitated by the addition of diethyl ether. The resulted precipitate is collected on a sintered glass crucible and washed thoroughly with diethyl ether and dried under vacuum.

c) Synthesis of [RuLL'(NCS)] where L is 4-(bis)ethylphosphonated-2,2':6',2"-terpyridine and L is 4,4'-dimethyl-2,2'-bipyridine 170 mg (0.27 mmol) of the product of Example 12b is dissolved in 20 ml of DMF under nitrogen. To this solution added 2 ml aqueous solution of NaNCS (300 mg, 3.7 mmol). After refluxing for 5 hours, the mixture is cooled and filtered through sintered glass crucible. The solution is concentrated to 5 ml on a rota-vap. To this concentrated solution, dichloromethane is added and a dense precipitate formed. The resulted precipitate is cooled on sintered glass crucible and washed with CH$_2$Cl$_2$ followed by water and dried under vacuum.

EXAMPLE 13 a) Synthesis of [RuL(Cl)$_3$] where L is selected form L$_j$ where R is hydrogen or C$_{1-15}$ alkyl group. This is prepared by an analogous procedure to that described in example 11a and using appropriate reagents.

b) Synthesis of [RuLL'(Cl)] where L is selected from L where R is hydrogen or C$_{1-15}$ alkyl and L' is selected from L$_a$ where R is ethyl This is prepared by an analogous procedure to that described in Example 12b using appropriate reagents.

c) Synthesis of [RuLL'(NCS)] where L is selected from L$_j$ where hydrogen or C$_{1-15}$ alkyl group and L' is selected from L$_a$ where R is ethyl This is prepared by an analogous procedure to that described in Example 12c using appropriate reagents.

EXAMPLE 14

Synthesis of [L$_2$Ru[NCRuL'$_2$(CN)$_2$] where L is selected from the ligand La and L' is selected from the ligand L$_f$ where R is hydrogen or C$_{1-15}$ alkyl group a) Synthesis of [RuL$_2$(Cl)$_2$] where L is selected from the ligand L$_a$ where R is ethyl. This is prepared by an analogous procedure to that described in Example 5a using appropriate reagents.

b) Synthesis of [RuL$_2$(Cl)$_2$] where L is selected from the ligand L$_f$ where R is hydrogen or C$_{1-15}$ alkyl group. This is prepared by an analogous procedure to that described in example 5a using appropriate reagents.

c) Synthesis of RuL$_2$(CN)$_2$] where L is selected from ligand L$_f$ where R is hydrogen or C$_{1-15}$ alkyl group. This is prepared by an analogous procedure to that described in Example 5c using appropriate reagents.

d) Synthesis of L$_2$Ru(NCRuL'$_2$(CN))$_2$] where L is selected from the ligand L$_a$ where R is ethyl and L' is selected from the ligand L$_f$ where R is hydrogen or C$_{1-15}$ alkyl group This is prepared by reacting one equivalent of the product of Example 14a and 2.5 equivalent of the product of Example 14c in DMF under nitrogen, for 5–8 hours. The required complex is precipitated by the addition of acetone/diethyl ether mixture and purified on alumina column, using ethanol as an eluent.

EXAMPLE 15

Synthesis of [LRu{NCRuL'$_2$(CN)}$_3$] where L is selected from the ligand L$_e$ where R is ethyl and L' is selected from the ligand L$_f$ where R is methyl a) Synthesis of [RuL(Cl)$_3$] where L is diethyl-2,2':6',2"-terpyridine4'-phosphonate. This is prepared by an analogous procedure to that described in Example 10a using appropriate reagents.

b) Synthesis of [RuL'$_2$(CN)$_2$] where L is selected from the ligand L$_f$. This is prepared by an analogous procedure to that described in Example 5c using appropriate reagents.

c) Synthesis of [LRu{NCRuL'$_2$(CN)}$_3$] where L is diethyl-2,2':6',2"-terpyridine4'-phosphonate and L' is selected from the ligand L$_f$ where R is methyl. This is prepared by reacting one equivalent of the product of Example 15a and 3.5 equivalents of the product of Example 15b in DMF under nitrogen, for 5–8 hours. The require complex is precipitated by the addition of acetone/diethyl ether mixture and purified on alumina column, using ethyl alcohol as an eluent.

All the complexes of ruthenium with phosphonated polypyridyl ligands gave satisfactory elemental analysis.

In the ligand L$_a$ to L$_j$ referred to in the Examples, unless indicted to the contrary, each R is hydrogen.

Application Example A

A photovoltaic device shown in FIG. 1 and based on the sensitization of an aluminum-doped titanium dioxide film supported on conducting glass is fabricated as follows:

A stock solution of organic titanium dioxide precursor is prepared by dissolving 21 mmol of freshly distilled TiCl$_4$ in 10 mL of absolute ethanol. TiCl$_4$ in ethanol solution gives titanium alkoxide spontaneously which, on hydrolysis, gives TiO$_2$. The stock solution is then diluted with further absolute ethanol to give two solutions (solution A and solution B having) titanium contents of 25 mg/ml (solution A) and 50 mg/ml (solution B). A third solution (C) is prepared from solution B by addition of AlCl$_3$ to yield an aluminium content of 1.25 mg/ml. A conducting glass sheet provided by Asahi Inc. Japan, surface area 10 cm$^2$ and having a visible light transmittance of at least 85% and a surface resistance smaller than 10 ohms per square cm is used as support for a deposited TiO$_2$ layer. Prior to use, the glass is cleaned with alcohol. A droplet of solution A is spread over the surface of the conducting glass to produce a thin coating. Subsequently the layer is hydrolyzed at 28° C. for 30 minutes in a special chamber, where the humidity is kept at 48% of the equilibrium saturation pressure of water. Thereafter, the electrode is heated in air in a tubular oven kept at 450° C., preheating it in the entrance of the oven for 5 minutes followed by 15 minutes of heating in the interior. Three more layers are produced in the same way. Subsequently, 5 thicker layers are deposited by using solution B. The same procedure as for the first layers is applied. Finally, solution C is used to deposit the last two layers containing the aluminum dopant. The heating of the last layer in the tubular oven is extended from 15 to 30 minutes. The total thickness of the titanium dioxide film is between 10 and 20 microns.

Prior to deposition of the dye, the film is subjected to a sintering treatment in highly purified 99.997% argon. A horizontal tubular oven composed of quartz tubes with suitable joints is employed. After insertion of the glass sheet with the $TiO_2$ film, the tube is twice evacuated and purged with argon. The glass sheet is then heated under argon flux at a flow rate of 2.5 L/h and a temperature gradient of 500° C./h up to 550° C. at which temperature it maintained for 35 minutes. This treatment produces anatase films with a surface roughness factor of 80–200.

After cooling under a continuous argon flow, the glass sheet is immediately transferred to an alcoholic solution (or alcohol/dimethylsulfoxide mixture) of a chromophore. The chromophore employed is the complex of Example 2. Its concentration in absolute ethanol is $5 \times 10^{-4}$M. Prolonged exposure of the film to the open air prior to dye adsorption is avoided in order to prevent hydroxylation of the $TiO_2$ surface as the presence of hydroxyl groups at the electrode surface interferes with dye uptake. The adsorption of chromophore from the ethanolic solution is allowed to continue for 30 minutes after which time the glass sheet is withdrawn and washed briefly with absolute ethanol. The $TiO_2$ layer on the sheet assumed a deep red colour owing to the chromophore coating.

Figure 2:
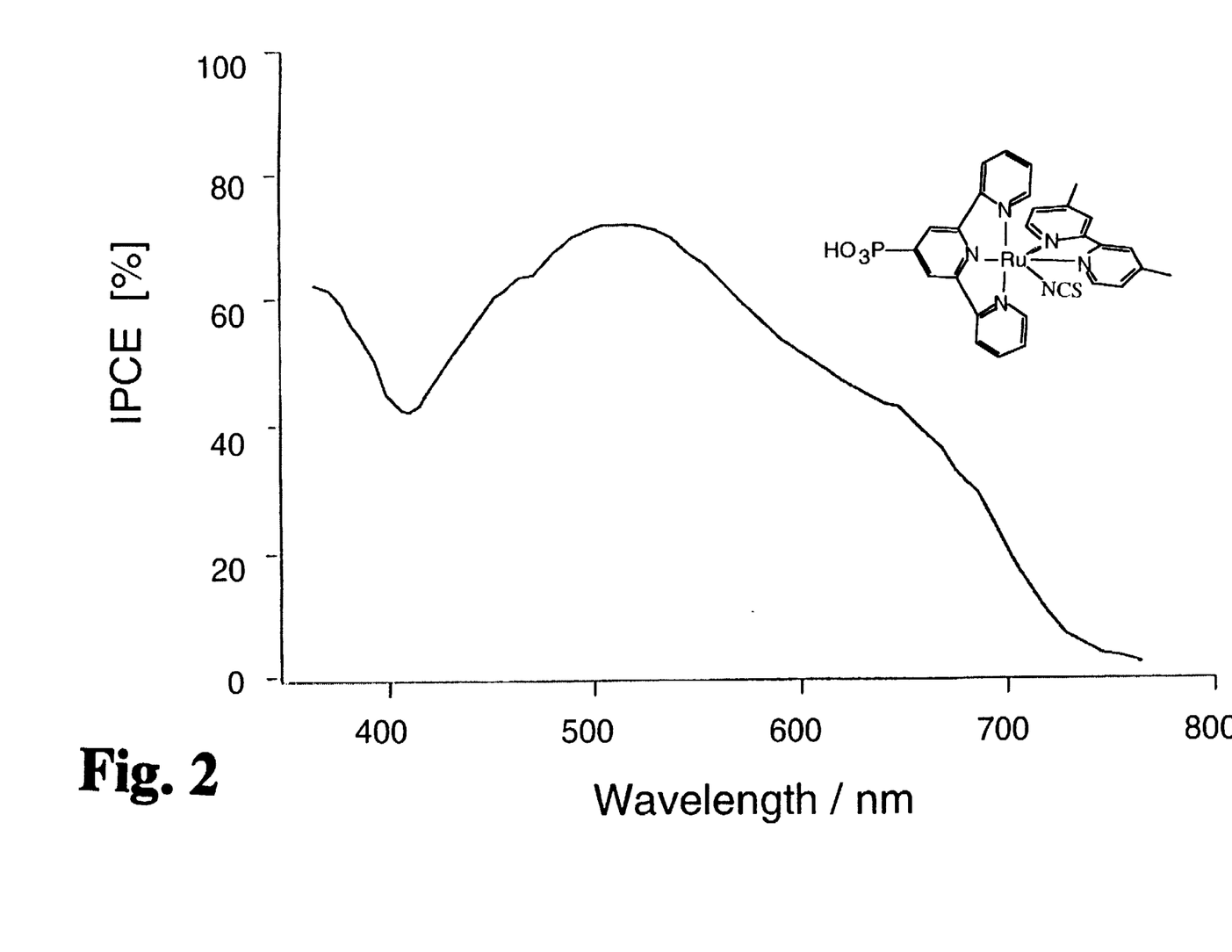
FIG. 2 is a photocurrent action spectrum.

The photocurrent action spectrum obtained with such a film using a conventional three electrode electrochemical cell containing an ethanolic solution of 0.5M LiI and $3 \times 10^{-3}$M iodine is shown in the attached figure together with the AM 1 spectral distribution of solar light emission. The incident monochromatic photon to current conversion efficiency (IPCE) is plotted as a function of the excitation wavelength. This was derived from the equation:

$$IPCE\,(\%) = \frac{[(1.24 \times 10^3) \times \text{photocurrent density } (\mu A/cm^2)]}{[\text{wavelength (nm)} \times \text{photon flux } (W/m^2)]} \quad (1)$$

From the overlap of the photocurrent action spectrum with solar emission the overall efficiency for the conversion of solar light to electricity η is calculated from the formula $$\eta = ISC \times OCV \times FF/P \quad (2)$$

where OCV is the open circuit voltage, ISC is the short circuit photocurrent density, FF is the fill factor of the photovoltaic cell and P is the incident solar light power.

For experimental verification of equation 2, a photovoltaic cell, shown in the drawing attached, is constructed, using the dye of Example 1 (4)-loaded $TiO_2$ (5) film supported on a conducting glass (the working electrode) comprising a transparent conductive tin dioxide layer (6) and a glass substrate (7) as a photoanode. The cell has a sandwich-like configuration, the working electrode (4–7) being separated from the counter electrode (1,2) by a thin layer of electrolyte (3) having a thickness of ca. 20 microns. The electrolyte used is an ethanolic solution of 0.5M LiI and $3 \times 10^{-3}$M iodine. The electrolyte (3) is contained in a small cylindrical reservoir (not shown) attached to the side of the cell from where capillary forces attract it to the interelectrode space. The counter-electrode comprises the conductive tin dioxide layer (2) deposited on a glass substrate (1) made also of Asahi conducting glass and is placed directly on top of the working electrode. A monomolecular transparent layer of platinum is deposited on to the conducting glass of the counter electrode (1,2) by electroplating from an aqueous hexachloroplatinate solution. The role of the platinum is to enhance the electrochemical reduction of iodine at the counter electrode. The transparent nature of the counterelectrode is an advantage for photovoltaic applications since it allows the harvesting of light from both the forward and the backward direction. Experiments are carried out with a high pressure Xenon lamp equipped with appropriate filters to simulate AM1 solar radiation. The intensity of the light is varied between 50 and 600 Watts per square meter and the open circuit voltage is 660 and 800 mV, respectively at these two voltages. The fill factor defined as the maximum electric power output of the cell divided by the product of open circuit voltage and short circuit current is between 0.7 and 0.75 V. A single crystal silicon cell gave an open voltage of 550 mV at 600 $W/M^2$ incident light intensity which dropped to below 300 mV at 50 $W/m^2$. This clearly shows that the cell of the present invention has a higher open circuit voltage than the silicon solar cell and that the open circuit voltage is less dependent on light intensity than that of the silicon cell. This constitutes a significant advantage for the use of such a cell in indirect sunlight or cloudy weather conditions. The fill factor of the silicon cell is comparable to that of the example. The overall solar light to electricity conversion efficiency of the cell of the example is between 5 and 6% in agreement with predictions of equation 2.

Application Example B

A transparent $TiO_2$ film from colloidal titanium dioxide particles which are deposited on a conducting glass support and sintered to yield a coherent highly porous semiconducting film that is transparent and can be used instead of the $TiO_2$ layer film in Application Example A.

Colloidal titanium oxide particle of approximately 10 nm are prepared by hydrolysis of titanium isopropoxide as follows:

125 ml of titanium isopropoxide is added to a solution of 0.1M nitric acid in 750 ml of water whilst stirring. A precipitate of amorphous titanium dioxide is formed under these conditions. This is heated to 80° C. for approximately 8 hours, stirring vigorously, resulting in peptisation of the precipitate and formation of a clear solution of colloidal anatase. The anatase structure of the titanium dioxide particles is established by Raman spectroscopy. The sol is concentrated by evaporation of the solvent in vacuum at room temperature until a viscous liquid is obtained containing the colloidal particles. At this stage the nonionic surfactant TRITON X-100 (40% weight of $TiO_2$) is added to reduce cracking of the film when applied to a substrate.

The titanium dioxide films are formed by spin coating the concentrated sol on to a conducting glass substrate. Usually it is sufficient to apply 6 to 10 layers in order to obtain semiconductor membranes of sufficient surface area to give excellent visible light harvesting efficiencies after deposition of a monolayer of the sensitizer.

Low resolution electron microscopy confirms the presence of the three layer structure, the lowest being the glass support followed by the 0.5 micron thick fluorine-doped $SnO_2$ and the 2.7 micron thick titanium dioxide layer. High resolution electron microscopy reveals the $TiO_2$ film to be composed of a three dimensional network of interconnected particles having an average size of approximately 16 nm. Apparently, significant particle growth occurs during sintering.

The transparent $TiO_2$ films are tested in conjunction with a sensitizer, the dye of Example 2 regenerative cell for the generation of electricity from visible light. The results can be represented where the photocurrent under simulated sunlight (intensity ca 30 W/m$^2$) is plotted as a function of cell voltage.

Application Example C

A sheet of conducting glass (ASAHI) area resistance ca 10 Ohm/square cm) having a size of 2×9.6 cm$^2$ is coated with a colloidal titanium dioxide film according to the procedure of Example B. A total of 7 layers of TiO$_2$ colloid are deposited successively by spin coating and the film is subjected each time to calcination at 500° C. for 30 minutes. 30% (w/w) of TRITON X 405 surfactant is added in order to avoid cracking of the film.

The final thickness of the titanium dioxide film is 5 microns as determined from the optical interference pattern. It is important to note that the conducing glass sheet after deposition of the TiO$_2$ remains clear and transparent to visible and near infrared light. The transmission spectrum recorded on a conventional spectrophotometer shows that a fraction of more that 60% of the visible light in the wavelength region between 400 and 900 nm is transmitted through the film. A UV/visible absorption spectrum of the electrode can be obtained. It exhibits a flat feature in the visible due to light absorption and scattering by the conducting glass and the 5 nm thick TiO$_2$ film. The steeply rising part of the absorption below, 400 nm is due to the band gap absorption of the TiO$_2$. Immediately before coating with dyestuff, the film is fired for 1 hour at 500° C. The coating of TiO$_2$ with dyestuff is performed by immersing the glass sheet for 16 hours in an ethanolic (or alcohol/diemthylsulfoxide mixture) solution containing the complex of Example 2. After coating, the glass sheet displays an intensive dark red coloration. The optical absorption spectrum measured with a conventional UV/visible spectrophotometer shows the absorbance in the vicinity of 500 nm to exceed the value of 2. indicating that in this wavelength range more than 99%. of the photons are absorbed by the dyestuff deposited on to the titanium dioxide film.

It is important to note that, due to the high concentration of dyestuff, the porous film is capable of harvesting photons over a very broad spectral range extending from 450 to 850 nm.

After dye deposition, the glass sheet is cut into two parts each having a size of ca 9 cm$^2$. These sheets serve as working electrodes (photo-anodes) in the module whose assembly is described further below.

Transparent counterelectrodes are made of the same type of ASAHI conducting glass as the working electrodes. The counterelectrode is not coated with TiO$_2$. Instead, the equivalent of 10 monolayers of Pt is electrochemically deposited on to conducting glass. The transparent nature of the counterelectrode is not affected by the deposition of the Pt its transmission in the visible and near infrared remaining greater that 60%. The Pt acts as an electrocatalyst, enhancing the rate of reduction of the electron transfer mediator, i.e. triiodide, at the counterelectrode. Two ca. 1 mm deep and 1.5 mm wide and 20 mm long indentations are engraved into the surface of the counterelectrode close to the edges of the glass sheets. These serve as a reservoir for the electrolyte.

The counter electrode is placed directly on top of the working electrode to yield a sandwich-type configuration. After filling the reservoirs with electrolyte, the cell was sealed with epoxy resin. The wetting of the space between the two electrodes by the electrolyte occurs spontaneously by capillary action. The electrolyte is a solution of 0.5M tetrapropyl ammonium iodide and 0.02M iodine in ethanol. Two cell are fabricated in this way, each having a surface area of ca 9cm$^2$. Subsequently they are connected in series by electrically contacting the photoanode of one cell to the cathode of the second cell. In this way a module is constructed, having a total surface area of 18 cm$^2$.

Application Example D

Nanostructured TiO$_2$films are prepared by spreading a viscous dispersion of colloidal TiO$_2$ particles on a conducting glass support (Asahi TCO glass, fluorine-doped SnO$_2$ overlayer, transmission ca 85% in the visible, sheet resistance 8 Ohm/square cm) and subsequent heating under air for 30 min at 30°–450° C. (preferably 450° C.). Two methods of preparation of colloidal TiO$_2$ dispersions are employed.

a) The procedure of Application Example B is repeated except that the colloidal anatase particles are subjected to autoclaving for 12–18 hours prior to concentrating the sol. The autoclaving is performed at 230° to 240° C. After spreading the colloid on the conducting glass support and calcining at 450° C., a few monolayers of TiO$_2$ are electrodeposited onto the colloidal TiO$_2$ film from an aqueous Ti(III) solution followed by renewed annealing at 450° C. This treatment is found to improve significantly the short circuit photocurrent as well as the open circuit voltage of the solar cell. Low resolution electron microscopy confirms the presence of a three-layer structure, the lowest being the glass support followed by the 0.7 µm thick fluorine-doped SnO$_2$ and the 10 µm thick colloidal TiO$_2$ film. High resolution electro microscopy reveals the TiO$_2$ film to be composed of a three-dimensional network of interconnected particles having an average size of approximately 15 nm.

b) The second method for preparation of nanosturctured films (Method B) employed commerical TiO$_2$ (P25. Degussa AG. Germany, a mixture of ca 30% rutile and 70% anatase). This is produced by flame hydrolysis of TiCl$_4$ and consists of weakly aggregated particles.. The BET surface areas is 55 m$^2$/g. corresponding to a mean particle size of about 25 nm. In order to break the aggregates into separate particles, the powder (12 g) is ground in a porcelain mortar with a small amount of water (4 ml), containing acetylacetone (0.4 ml) to prevent reaggregation of the particles. Other stabilizers such as acids, bases or TiO$_2$ chelating agents are found to be suitable as well. After the powder has been dispersed by the high shear forces in the viscose paste it is diluted by slow addition of water (16 ml) under continued grinding. Finally, a detergent (0.2 ml Triton®X-100) is added to facilitate the spreading of the colloid on the substrate. The conducting TCO glass is covered on two parallel edges with adhesive tape (~40 µm thick) to control the thickness of the TiO$_2$ film and to provide noncoated area for electrical contact. The colloid (5 µl/cm$^2$) is applied to one of the free edges of the conducting glass and distributed with a glass rod sliding over the tape covered edges. After air drying, the electrode is fired for 30 minutes at 30°–550° C. (preferably 450°–550° C.) in air. The resulting film thickness is 12 µm but can be varied by changing the colloid concentration or the adhesive tape thickness.

The performance of the film, as sensitized photoanode, is improved by further deposition of TiO$_2$ from aqueous TiCl$_4$ solution. A 2M TiCl$_4$ stock solution is prepared at 0° C. to prevent precipitation of TiO$_2$ due to the highly exothermic hydrolysis reaction. This stock solution is freshly diluted with water to 0.2M $TiCl_4$ and applied onto the electrode (50 μl/cm$^2$). After standing overnight at room temperature in a closed chamber, the electrode is washed with distilled water. Immediately before dipping into the dye solution it is fired again for 30 minutes at 30°–550° C. (preferably 450°–550° C.) in air. Similarly to the electro-deposition from aqueous Ti(III) solution, this procedure results in the deposition of nano-sized $TiO_2$ particles on the $TiO_2$ film further increasing its active surface area. Furthermore, this treatment as well as the anodic deposition of $TiO_2$ from Ti(III) solution described above appears to lead to deposits having a very low impurity content. This is corroborated by the fact that the treatment becomes ineffective if the $TiCl_4$ solution is evaporated before firing instead of being washed off. Impurities in the $TiCl_4$, such as $Fe^{3+}$, are not deposited by hydrolysis from the acidic $TiCl_4$ solution due to the higher solubility of iron oxide compared to $TiO_2$. By contrast, the evaporation of the $TiCl_4$ solution results in the deposition of impurities. The P25 powder contains up to 100 ppm $Fe_2O_3$, which is known to interfere with electro-injection of the excited dye. The $TiCl_4$ treatment covers this rather impure core with a thin layer of highly pure $TiO_2$ improving the injection efficiency and the blocking character of the semi-conductor-electrolyte junction.

Coating of the $TiO_2$ surface with dyestuff is carried out by soaking the film for ca 3 h in a $3 \times 10^4$M solution of the ruthenium complex from Example 1 in dry ethanol (or alcohol/dimethylsulfoxide mixture). The dye coating is done immediately after the high temperature annealing in order to avoid rehydroxylation of the $TiO_2$ surface or capillary condensation of water vapor from ambient air inside the nanopores of the film. The presence of water in the pores decreases the injection efficiency of the dye. The electrode is dipped into the dye solution while it is was still hot, i.e. its temperature is ca 80° C. After completion of the dye adsorption, the electrode is withdrawn from the solution under a stream of dry air or argon. It is stored in dry ethanol or immediately wetted with the $LiI/LiI_3$ acetonitrile redox electrolyte for testing. The amount of adsorbed dye is determined by desorbing the dye from the $TiO_2$ surface into a solution of $10^{-4}$ NaOH in ethanol (or alcohol/dimethylsulfoxide mixture) and measuring its adsorption spectrum.

A BAS100 electrochemical analyzer (Bioanalytical Systems, USA) is used to perform cyclic voltametry in electrochemical cells of columns of 5 to 20 ml. A three-electrode cell is made up of a glassy carbon or Pt disc (3 mm diameter embedded in Teflon) working electrode and a platinum wire counter electrode. The reference electrode consists of calomel in contact with 0.1 LiCl in methanol. It is separated from the working electrode compartment by bridge containing the same electrolyte as the test solution, i.e. 0. 1M n-tetrabutylammonium perchlorate in acetonitrile or ethanol. All potentials indicated refer to the aqueous SCE electrode.

Photo-electrochemical experiments employed a similar cell equipped with a flat pyrex window. Alternatively, the dye sensitized $TiO_2$ film is incorporated into a thin layer sandwich type solar cell. A light reflecting counterelectrode is employed consisting of a conducting glass support onto which a 2 μm thick Pt mirror had been deposited by sputtering. The counterelectrode is placed directly on top of the dye coated transparent $TiO_2$ film supported by the conducting glass sheet. Both electrodes are clamped tightly together. A thin layer of electrolyte is attracted into the inter-electrode space by capillary forces. The dyed coated $TiO_2$ film is illuminated through the conducting glass support. The conversion efficiencies reported are overall yields which are uncorrected for losses due to light absorption and reflection by the conducting glass support. An Oriel 450W Xe lamp served as a light source in conjunction with a polycarbonate filter to remove ultraviolet radiation and a Schott a 113 interference filter to mimic AM 1.5-type solar emission.

The emission spectra are measured on a Spex Fluorolog II equipped with a 450 W Xenon light source. The measured excitation and emission spectra are routinely corrected for the wavelength-dependent features using correction factors generated by a National Bureau of Standards 150W halogen lamp. The emission detector is a Hamarnatsu R2658 photomultiplier which extends the corrected emission measurement over a region from 250 to 1000 nm. All solutions are prepared by dissolving the appropriate amount of complex in the desired solvent to give typically a $2 \times 10^{-5}$M solution. The solutions are degassed by freeze, pump and thaw methods. Low temperature measurements are carried out in an Oxford Instruments cryostat.

The emission lifetimes are measured by exciting the sample with active modelocked Nd YAG laser pulse, using the frequency doubled line at 532 nm. The emission decay is followed on a Tektronix DSA 602A Digitizing Signal Analyzer. The digitized xy data is subsequently analyzed and fitted to an exponential model. Sample concentrations were typically $1 \times 10^{-4}$M. Optical densities are taken from spectra recorded on a Cary 5 spectrophotometer.

Application Example E

Figure 1:
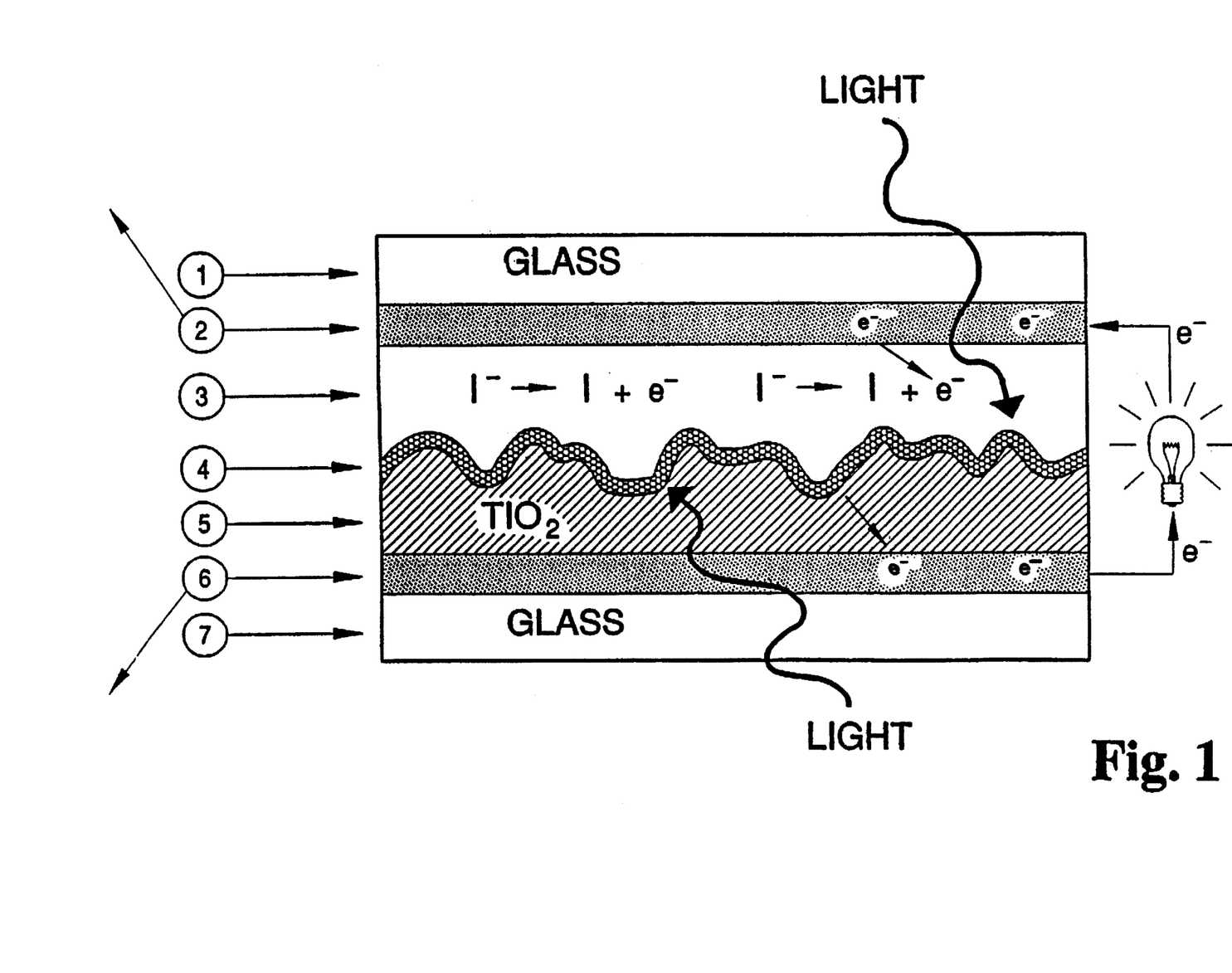
FIG. 1 is a photovoltaic cell based on the application of the compounds and complexes of the present invention.

A photovoltaic device shown in FIG. 1 based on the sensitization of a transparent $TiO_2$ film made from colloidal titanium dioxide particles which are deposited on a conducting glass support and sintered to yield a coherent highly porous semiconducting film.

Colloidal titanium oxide particles of approximately 8 nm are prepared by hydrolysis of titanium isopropoxide as follows:

125 ml titanium isopropoxide is added to a solution of 0.1M nitric acid in 750 ml water while stirring. A precipitate of amorphous titanium dioxide is formed under these conditions. This is heated to 80° C. for approximately 8 hours, stirring vigorously, resulting in peptisation of the precipitate and formation of a clear solution of colloidal anatase. The propanol formed by the hydrolysis is allowed to evaporate during the heating. The colloidal solution is then autoclaved at 230° to 240° C., in a pressure vessel of titanium metal or teflon for 2 to 20 hours, preferably 16 hours. The resultant sol, containing some precipitate is stirred or shaken to resuspend the precipitate. The resulting sol, minus any precipitate that will not resuspend, is concentrated by evaporation of the solvent in vacuum at room temperature until a viscous liquid is obtained containing the colloidal particles. A typical concentration at this point is 200 g/L. At this stage a polyethylene oxide polymer, for example Union Carbide Carbowax 20M or Triton X-405 can be added to increase the thickness of the layer that be deposited without cracks. The polymer is added in amount of 30 to 50, preferably 40, weight percent $TiO_2$.

The electrodes for sensitization are formed from the colloidal solution as follows:

A suitable substrate, for example a 3×6 cm piece of conductive tin oxide coated glass, for example from Asahi Corp. (but also titanium metal or any flat conductive surface), is placed with the conductive surface up and with suitable spacers, for example 50 to 100 micron, preferably 80 micron thick plastic tape, placed along each edge. A suitable amount of the sol, for example 150 microliters of sol with 200 g/L $TiO_2$ and 40% Carbowax 20M for the above substrate, is pipetted along one end of the substrate. The sol is spread across the substrate by drawing with a flat edged piece of glass whose ends ride along the spacers. Thus the spacers, the viscosity of the sol, and the concentration of the sol control the amount of $TiO_2$ deposited.

The film is spread and allowed to dry in room air till visibly dry and preferable and additional 20 minutes. After drying the electrode is fired at 400° to 500° C., preferably 450, for a minimum of 20 minutes. In the case of sols autoclaved below 170° C. the spacers less than 40 micron must be used and the process must be repeated twice to achieve an 8 to 10 micron thick $TiO_2$ film.

Electrodes of up to 10 cm by 10 cm have been fabricated by this method. The sol can also be applied to substrates by spin coating and dip coating.

The electrode can then be cut to the size desired by normal glass cutting techniques. Immediately before applying the sensitizer the electrode is fired again at 450 to 550, preferably 500° C. for 2 to 12, preferably 6 hours. For some solvent and dye combinations the surface of the electrode is improved (with respect to electron injection) by firing the electrode 5 to 10, preferably 7 times at 500° C. for 2 to 6 hours with either 10 hours in air or soaking up to 1 hour in water, 0.5M nitric acid or 0.5M HCl, between each firing. The acid solutions are saturated with dissolved $TiO_2$ before use. After the last firing, immediately after cooling, the electrode is placed in the sensitizer solution. Preferably an ethanolic (or alcohol/dimethylsulfoxide mixture) solution containing the complex of Example 1 is made up. Depending on the sensitizer between 4 and 24 hours are required for the electrode to gain full color. Full color can be estimated by eye or by taking visible light transmittance spectra of the dye at various time.

After removal from the dye solution, the electrode is made into a photovoltaic cell as follows:

Transparent counterelectrodes are made of the same type of ASAHI conducting glass as the working electrodes. The counterelectrode is not coated with $TiO_2$. Instead the equivalent of 10 monolayers of Pt is electrochemically deposited onto conducting glass. The transparent nature of the counterelectrode is not affected by the deposition of the Pt, its transmissions is visible and near infrared remains greater that 60%. The Pt acts as an electrocatalyst enhancing the rate of reduction of the electron transfer mediator, i.e. triiodide, at the counterelectrode.

Alternatively, a thin titanium sheet, which may be porous coated as above with Pt, may be used as a counter electrode. In the case of a porous sheet, another sheet of impervious material is required behind the counter electrode, such as plastic, glass or metal.

A reservoir is provided for the electrolyte by engraving two ca 1 mm deep and 1.5 mm wide and 20 mm long clefts into the surface of the counterelectrode close to the edges of the glass sheet. The reservoir can also be added external to the glass sheets or be behind the counter electrode in the case of porous counter electrode.

The countereletrode is place directly on top of the working electrode to yield a sandwich type configuration. The reservoirs are filled with electrolyte solution, selected from the list above buy preferably 85% by weight ethylene carbonate, 15% propylene carbonate 0.5M potassium iodide and 40 mM iodine. An amount of LiI or tetraalkylammonium iodide can be present (preferably 20 mM) depending on the voltage desire. The cell is sealed around the edge with a sealant compatible with the solvent chosen and bonded-closed with an adhesive. The sealant and the adhesive may be the same material for example silicon adhesive in the case of the alcohol solvents, or for example, polyethylene and epoxy resin (or mechanical closure) in the case of ethylene carbonate. The wetting of the space between the two electrodes by the electrolyte injected into the reservoirs occurs spontaneously by capillary action.

Application Examples A to E can be repeated using instead to the compound of Example 2, the same amount of the ruthenium dyes of Examples 4 to 15.

We claim:

1. A compound, in metal-free form, of formula 1 to 3

(1)

(2)

(3)

In which

R is hydrogen or $C_{1-30}$ alkyl;

X is hydrogen, halogen (preferably Cl or Br) or $C_{1-30}$ alkyl.

* * * * *

UNITED STATES PATENT AND TRADEMARK OFFICE
CERTIFICATE OF CORRECTION

PATENT NO. : 5,789,592
DATED : August 4, 1998
INVENTOR(S) : GRATZEL, Michael et al.

It is certified that error appears in the above-identified patent and that said Letters Patent is hereby corrected as shown below:

In column 1, line 6, please change "PCT/11394/00088" to --PCT/IB94/00088--.

In column 12, line 57, please change "$^{284}$" to --284--.

In column 13, line 3, please change "Le" to --$L_e$--.

In column 13, line 34, please change "dichloromethane" to --dichloromethane--

In column 16, line 8, please change "AMI" to --AM1--.

Signed and Sealed this

Twentieth Day of April, 1999

Q. TODD DICKINSON

*Attest:*

*Attesting Officer*   Acting Commissioner of Patents and Trademarks